United States Patent
Odidi et al.

(10) Patent No.: US 6,607,751 B1
(45) Date of Patent: Aug. 19, 2003

(54) CONTROLLED RELEASE DELIVERY DEVICE FOR PHARMACEUTICAL AGENTS INCORPORATING MICROBIAL POLYSACCHARIDE GUM

(75) Inventors: Isa Odidi, Mississauga (CA); Amina Odidi, Mississauga (CA)

(73) Assignee: Intellipharamaceutics Corp., Mississauga (CA)

(*) Notice: Subject to any disclaimer, the term of this patent is extended or adjusted under 35 U.S.C. 154(b) by 0 days.

(21) Appl. No.: 09/169,409

(22) Filed: Oct. 9, 1998

Related U.S. Application Data

(60) Provisional application No. 60/061,501, filed on Oct. 10, 1997.

(51) Int. Cl.[7] .............................. A61K 9/22; A61K 9/24; A61K 9/10; A61K 9/16; A61K 47/36
(52) U.S. Cl. ........................ 424/488; 424/485; 424/468; 424/472; 424/499; 514/961
(58) Field of Search .................................. 424/464, 485, 424/488, 494, 472, 451, 457, 468; 514/960, 962, 961

(56) References Cited

U.S. PATENT DOCUMENTS

| | | | |
|---|---|---|---|
| 3,845,770 A | | 11/1974 | Theeuwes et al. .......... 128/260 |
| 3,916,899 A | | 11/1975 | Theeuwes et al. .......... 128/260 |
| 4,016,880 A | | 4/1977 | Theeuwes et al. .......... 128/260 |
| 4,160,452 A | | 7/1979 | Theeuwes .................... 128/260 |
| 4,200,098 A | | 4/1980 | Ayer et al. ................... 128/260 |
| 4,756,911 A | * | 7/1988 | Drost et al. |
| 4,832,958 A | * | 5/1989 | Baudier et al. |
| 5,240,712 A | * | 8/1993 | Smith et al. |
| 5,415,871 A | * | 5/1995 | Pankhania et al. |
| 5,472,711 A | * | 12/1995 | Baichwal |

* cited by examiner

*Primary Examiner*—Edward J. Webman
(74) *Attorney, Agent, or Firm*—Foley Hoag LLP

(57) ABSTRACT

The present invention provides a controlled release device for sustained or pulsatile delivery of pharmaceutically active substances for a predetermined period of time. This invention further provides such device in which sustained or pulsatile delivery is obtained by the unique blend and intimate mixture of pharmaceutically active substances with a microbial polysaccharide and uncrosslinked linear polymer and optionally a crosslinked polymer and/or lipophillic polymer and/or lipophillic polymer and/or saturated polyglycolyzed glyceride. The invention also provides for the manufacture of such devices and pharmaceutical compositions containing the same.

20 Claims, No Drawings

CONTROLLED RELEASE DELIVERY DEVICE FOR PHARMACEUTICAL AGENTS INCORPORATING MICROBIAL POLYSACCHARIDE GUM

This application claims the benefit of Provisional application Ser. No. 60/061,501, filed Oct. 10, 1997.

FIELD OF THE INVENTION

The present invention relates to a controlled release device which provides sustained or pulsatile delivery of pharmaceutically active substances for a predetermined period of time. This invention further relates to such device in which sustained or pulsatile delivery is obtained by the unique blend and intimate mixture of pharmaceutically active substances with a microbial polysaccharide and uncrosslinked linear polymer and optionally a crosslinked polymer and/or lipophillic polymer and/or saturated polyglycolyzed glyceride. The invention also relates to a process for the manufacture of such devices and pharmaceutical compositions containing the same.

BACKGROUND OF THE INVENTION

The prior art teaches many systems for the delivery of pharmaceutically beneficial agents. One such system operates by means of an osmotic pumping mechanism. However, it suffers from being very complex and is complicated to manufacture. A second type of pharmaceutical delivery system utilizes hydrogels either from a group consisting of uncrosslinked linear polymers or from a group consisting of crosslinked polymers. In devices using uncrosslinked polymers, viscosity is the rate controlling factor for drug release kinetics. In these systems a gelatinous layer is formed on the surface upon hydration. The thickness and durability of this gelatinous layer depends upon the concentration, as well as the molecular weight and viscosity of the polymer in the device. At higher concentrations the linear polymer chains entangle to a greater degree leading to virtual crosslinking and a stronger gel layer. Drug release is by the dissolution of polymer and erosion of the gel layer and hence the rate of erosion is what controls the release rate. Although viscosity is an important consideration in controlled drug release from hydrogel matrices, it is viscosity under low shear conditions that control diffusion through the matrix.

Several U.S. Patents are directed to the various pharmaceutical delivery systems as mentioned above, see for example U.S. Pat. Nos. 3,845,770, 3,916,899, 4,016,880, 4,160,452 and 4,200,098. While these systems do provide for the delivery of a selected pharmaceutical agent, none of these provide a controlled or pulsatile delivery of the pharmaceutical agent in which drug release is modulated by combining a microbial polysaccharide and uncrosslinked polymer. Furthermore, none of the prior art teaches a device comprising a microbial polysaccharide and uncrosslinked polymer and optionally a crosslinked polymer and/or lipophillic polymer and/or saturated polyglycolyzed glyceride.

There was therefore a need to develop a novel controlled release pharmaceutical delivery device which could be made in a cost efficient manner and provide for either sustained or pulsatile delivery of the selected pharmaceutical incorporated therein.

SUMMARY OF THE INVENTION

It is an object of the present invention to provide a novel controlled pharmaceutical release device capable of delivering in a controlled, continuous or pulsatile manner therapeutically effective amounts of pharmaceutically active agent for a predetermined period of time in mammals, especially human beings.

According to an object of the present invention is a controlled pharmaceutical release device for use with a selected pharmaceutical to provide continuous or pulsatile therapeutically effective amounts of the pharmaceutical, the device comprising;

about 1 to 60% by weight microbial polysaccharide; and
about 1 to 60% by weight uncrosslinked linear polymer.

The device may optionally comprise about 1 to 50% by weight crosslinked polymer, about 1 to 50% by weight lipophillic polymer and/or 1 to 50% by weight saturated polyglycolyzed glyceride.

According to another object of the present invention is a pharmaceutical composition which provides controlled release of the pharmaceutical contained therein, said composition comprising;

about 1 to 60% by weight microbial polysaccharide;
about 1 to 60% by weight uncrosslinked linear polymer; and
about 1 to 80% by weight pharmaceutical active.

The composition may optionally comprise about 1 to 50% by weight crosslinked polymer, about 1 to 50% by weight lipophillic polymer and/or 1 to 50% by weight saturated polyglycolyzed glyceride. According to yet a further object of the present invention is a method for making a controlled release formulation of pharmaceutically active agents, said method comprising:

blending about 1 to 80% by weight pharmaceutical active with about 1 to 60% by weight microbial polysaccharide and about 1 to 60% by weight uncrosslinked linear polymer to form a homogeneous blend;

granulating said homogeneous blend and kneading to form wet granules;

drying the wet granules to a loss on drying of about <5%;

size reducing the dried granules to provide a granule size of about <1400 microns;

blending the dried granules with about 0.5 to 10% lubricant; and compressing the lubricated granules into tablets.

Preferably, the pharmaceutically active agent is intimately mixed with a microbial polysaccharide and uncrosslinked linear polymer and further wet granulated, dried, sieved, lubricated and pressed into tablets.

Optionally, to the mixture of pharmaceutical active, microbial polysaccharide and uncrosslinked linear polymer may be added about 1 to 50% by weight crosslinked polymer, about 1 to 50% by weight lipophillic polymer and/or 1 to 50% by weight saturated polyglycolyzed glyceride.

In a further aspect of this invention there is provided a method for delivering soluble or poorly soluble pharmaceutically active agents by deliberate and expert manipulation of the composition and ratios of a microbial polysaccharide, preferably xanthan gum, and uncrosslinked linear polymer, preferably hydroxypropylmethyl cellulose polymers, present in the device. The composition and ratios of the optional crosslinked polymer, preferably Carbopol 971P, and/or lipophillic polymer, preferably glyceryl behenate, and/or saturated polyglycolyzed glyceride, preferably gelucire 44/14, may also be manipulated to vary the type of release provided.

DETAILED DESCRIPTION OF THE PREFERRED EMBODIMENTS

The novel controlled delivery device of the present invention provides the controlled release of a selected pharmaceutically active agent in a sustained or a pulsatile manner. In one embodiment, the device is formulated as a composition comprising pharmaceutically active agents in a sustained release matrix tablet. In another embodiment, a method is provided for making the controlled release pharmaceutical delivery device.

The present invention is simple in fabrication, permitting efficient and reproducible mass production by conventional techniques.

The device comprises a mixture of about 1 to 60% by weight uncrosslinked linear polymers and about 1 to 60% by weight microbial polysaccharides to which about 1 to 80% by weight selected pharmaceutical active is added. Suitable pharmaceuticals for use in the device include but are not restricted to diltiazem, glipizide, buspirone, tramadol, gabapentin, verapamil, etodolac, naproxen, diclofenac, COX2 inhibitors, budesonide, venlafaxine, metoprolol, carbidopa, levodopa, carbamazepine, ibuprofen, morphine, pseudoephedrine, paracetamol, cisapride, pilocarpine, methylphenidine, nifedipine, nicardipine, felodipine, captopril, terfenadine, pentoxifylline, fenofibrate, aciclovir, zidovudine, moclobemide, potassium chloride, lamotrigine, citalopram, cladribine, loratadine, pancrelipase, lithium carbonate, orphenadrine, ketoprofen, procainamide, ferrous sulfate risperidone, clonazepam, nefazodone, lovastatin, simvastatin, pravachol, ketorolac, hydromorphone, ticlopidine, seligiline, alprazolam, divalproex and phenytoin.

Uncrosslinked linear polymers suitable for use in the present invention are cellulose ethers preferably hydroxypropylmethyl cellulose (HPMC). Suitable microbial polysaccharides for use in the invention include xanthan gum.

The device may optionally comprise about 1 to 50% by weight crosslinked polymer, preferably Carbopol 971P, about 1 to 50% by weight lipophillic polymer, preferably glyceryl behenate, glyceryl palmitostearate or glyceryl, and/or 1 to 50% by weight saturated polyglycolyzed glyceride, preferably gelucire 44/14.

The device may optionally include about 0.5 to 10% by weight lubricants such as for example magnesium stearate and/or talc as well as about 0.5 to 10% by weight granulating or tabletting aids such as silicone dioxide, microcrystalline cellulose, calcium phosphate, sodium laurel sulphate, calcium sulphate and silicified microcrystalline cellulose.

The device can be fabricated with any suitable pharmaceutical active as a tablet, a film coated tablet or a capsule for easy ingestion.

It was unexpectedly found that controlled delivery devices comprising xanthan gum and uncrosslinked linear polymers together in an intimate mixture with a pharmaceutically active agent perform efficient and optimal controlled release of the pharmaceutical active than if either polymer were to be used alone. It was also found that such delivery devices when additionally comprising crosslinked polymers and/or lipophillic polymers and/or saturated polyglycolyzed glyceride also provides efficient controlled release of the pharmaceutical active contained therein. Uncrosslinked linear polymers such as hydroxypropylmethyl cellulose (HPMC) tend to become more newtonian at low shear and the viscosity becomes independent of shear rate. Xanthan gum on the other hand displays a pseudoplastic nature in which there is a linear dependence of viscosity as a function of the shear rate. At low shear rates xanthan gum has higher viscosity compared to hydroxypropylmethyl cellulose (these differences are larger at even lower shear rates) while the opposite is the case at higher shear rates. During transit in the gastrointestinal tract (GIT) a matrix controlled delivery device encounters regions of turbulence and non turbulence. It is hypothesized that regions of non turbulence present lower shear rates to the matrix tablets, conditions for which xanthan gum demonstrates higher viscosity than HPMC while regions of turbulence present higher shear rates to the matrix tablet, conditions for which HPMC demonstrate a higher viscosity than xanthan gum. Since matrix devices rely on the development of a viscous layer around the tablet to control diffusion of the drug from the surface and interior of the tablet, the use of xanthan gum alone in a matrix tablet will presumably be more efficient in regions of non turbulence while HPMC matrices will be more efficient in regions of turbulence. However, since these tablets encounter both environmental conditions, a controlled delivery device comprising of both xanthan gum and HPMC together in intimate mixture with the pharmaceutically active agent(s) will provide optimum controlled performance.

According to one embodiment of the present invention is the preferred form of the sustained release device which is presented as a matrix tablet that is prepared using the following steps:

Step 1. Intimately blending a pharmaceutically active agent (s) (about 1–80% by weight) with about 1–60% by weight of xanthan gum and about 1–60% by weight of hydroxypropylmethyl cellulose (preferably Methocel™ premium grade type K100M CR or K4M CR) in a planetary or high shear mixer.

Step 2. Granulating the homogeneous blend from step 1 with a granulating solution (preferably isopropyl alcohol) in a planetary or high shear mixer. It is preferable to knead the wet mass for about 1–3 minutes after wet granulation.

Step 3. Drying the wet granules in a fluid bed dryer or tray dryer to a loss on drying (LOD) of about <5%. Preferably they are dried in a tray dryer at about >40° C. to an LOD of about <2%.

Step 4. Size reduction of the dried granules from step 3 is done in a mill, preferably a Cone mill, such that granule size is about <1400 microns.

Step 5. Intimately blending the milled granules with about 0.5–10% by weight of magnesium stearate and/or about 0.5 to 10% by weight talc in a V-blender.

Step 6. The lubricated granules from step 5 are compressed into tablets using a rotary tablet press. The resulting tablets have a hardness of about >5 Strong Cobb units and a friability of about <1%.

Step 7. Optional Other granulating or tabletting aids such as silicone dioxide, microcrystalline cellulose and calcium phosphate can be added into step 5.

Step 8. Optional The tablet produced in step 6 can be film coated with a suitable coating. Such coatings are well known in the art of pharmaceuticals. One skilled in the art would readily comprehend the type of film coating materials and quantity that may be used in the present invention.

Depending upon the conditions under which the materials are processed and the depending on the relative proportions of the several components, one obtains a product of unique sustained release characteristics. The sustained release characteristic of the composition can be predetermined and varied by adjusting the makeup of the composition within the aforesaid limits. The duration, uniformity and continuity of release of the pharmaceutically active agent(s) can be suitably controlled by varying the relative amount of the xanthan gum and HPMC.

Pulsatile delivery is achieved by making a unit dose such as a capsule containing a plurality of tablets or population of granules which release the active agent at different rates or at different time intervals so that, for example, if one tablet or population of granules starts releasing first and reaches a peak, another can start and peak as the previous one is declining. This results in pulsatile delivery.

For a sustained release effect one population or a uniform matrix is used which releases the pharmaceutical active gradually. A desired rate is obtained by manipulating quantities in the composition.

When the delivery device of this invention is administered to the gastrointestinal tract by oral route it comes into contact with an aqueous environment and hydrates forming a gelatinous layer. During transit in the gastrointestinal tract it encounters regions of non turbulence and turbulence which presents lower shear rates and higher shear rates respectively. Matrix devices rely on the development of a viscous layer around the tablet to control diffusion of the drug from the surface and interior of the tablet. On a comparative basis xanthan gum gives higher viscosity at lower shear rates and HPMC give higher viscosity at higher shear rates. Therefore, the use of either xanthan gum or HPMC alone in a matrix tablet will not give an optimum performance when compared to matrix tablets comprising of both xanthan gum and HPMC together in intimate mixture with the pharmaceutically active agent(s). The present invention consist of a controlled delivery device capable of optimum performance in the GIT in which the active agent is in intimate mixture with both xanthan gum and HPMC and optionally crosslinked polymer and/or lipophillic polymer and/or saturated polyglycolyzed glyceride in a matrix.

EXAMPLES

The examples are described for the purposes of illustration and are not intended to limit the scope of the invention.

Methods of synthetic chemistry, pharmacy and pharmacology referred to but not explicitly described in this disclosure and examples are reported in the scientific literature and are well known to those skilled in the art.

Example 1

Diltiazem Hydrochloride ER Tablets

|  | % composition |
| --- | --- |
| Diltiazem hydrochloride | 30 |
| Xanthan gum | 30 |
| Hydroxypropylmethyl cellulose K100M CR | 38 |
| Talc | 1 |
| Magnesium stearate | 1 |

Diltiazem hydrochloride was blended with xanthan gum and hydroxypropylmethyl cellulose in a high shear mixer until a homogeneous mixture was obtained. The mixture was granulated with isopropyl alcohol and dried in fluid bed dryer to a loss on drying of about <2.0%. The dried granules were passed through a sieve #14 mesh. The milled granules were blended with talc and magnesium stearate for 5 minutes in a V-blender. Finally, the treated granules were pressed into tablets using a rotary tablet press.

Example 2

Diltiazem Hydrochloride ER Tablets

|  | % composition |
| --- | --- |
| Diltiazem hydrochloride | 30 |
| Microcrystalline cellulose | 10 |
| Xanthan gum | 25 |
| Hydroxypropylmethyl cellulose K100M CR | 33 |
| Talc | 1 |
| Magnesium stearate | 1 |

Diltiazem hydrochloride was blended with microcrystalline cellulose, xanthan gum and hydroxypropylmethyl cellulose in a high shear mixer until a homogeneous mixture was obtained. The mixture was granulated with isopropyl alcohol and dried in fluid bed dryer to a loss on drying of about <2.0%. The dried granules were passed through a sieve #14 mesh. The milled granules were blended with talc and magnesium stearate for 5 minutes in a V-blender. Finally, the treated granules were pressed into tablets using a rotary tablet press.

Example 3

Glipizide ER Tablet

|  | % composition |
| --- | --- |
| Glipizide | 4 |
| Microcrystalline cellulose | 20 |
| Xanthan gum | 40 |
| Hydroxypropylmethyl cellulose K100M CR | 33 |
| Silicone dioxide | 1 |
| Talc | 1 |
| Magnesium stearate | 1 |

Glipizide was blended with silicone dioxide, microcrystalline cellulose, xanthan gum and hydroxypropylmethyl cellulose in a high shear mixer until a homogeneous mixture was obtained. The mixture was granulated with isopropyl alcohol and dried in fluid bed dryer to a loss on drying of about <2.0%. The dried granules were passed through a sieve #14 mesh. The milled granules were blended with talc and magnesium stearate for 5 minutes in a V-blender. Finally, the treated granules were pressed into tablets using a rotary tablet press.

Example 4

Glipizide ER Tablet

|  | % composition |
| --- | --- |
| Glipizide | 4 |
| Microcrystalline cellulose | 20 |
| Xanthan gum | 40 |
| Hydroxypropylmethyl cellulose K4M CR | 33 |
| Silicone dioxide | 1 |
| Talc | 1 |
| Magnesium stearate | 1 |

Glipizide was blended with silicone dioxide, microcrystalline cellulose, xanthan gum and hydroxypropylmethyl cellulose in a high shear mixer until a homogeneous mixture was obtained. The mixture was granulated with isopropyl alcohol and dried in fluid bed dryer to a loss on drying of about <2.0%. The dried granules were passed through a sieve #14 mesh. The milled granules were blended with talc and magnesium stearate for 5 minutes in a V-blender. Finally, the treated granules were pressed into tablets using a rotary tablet press.

Example 5

Naproxyn Sodium ER Tablets

|  | % composition |
| --- | --- |
| Naproxyn sodium | 55 |
| Microcrystalline cellulose | 10 |
| Xanthan gum | 10 |
| Hydroxypropylmethyl cellulose K100M CR | 18 |
| Carbopol 971P NF | 5 |
| Talc | 1 |
| Magnesium stearate | 1 |

Naproxyn sodium was blended with microcrystalline cellulose, xanthan gum and hydroxypropylmethyl cellulose in a high shear mixer until a homogeneous mixture was obtained. This mixture was granulated with isopropyl alcohol and dried in fluid bed dryer to a loss on drying of about <2.0%. The dried granules were then passed through a sieve #14 mesh. The milled granules were blended with Carbopol 971P for 10 minutes, then with talc and magnesium stearate for 5 minutes in a V-blender. Finally, the treated granules were pressed into tablets using a rotary tablet press.

Example 6

Naproxyn Sodium ER Tablets

|  | % composition |
| --- | --- |
| Naproxyn sodium | 55 |
| Microcrystalline cellulose | 10 |
| Xanthan gum | 10 |
| Hydroxypropylmethyl cellulose K100M CR | 14 |
| Gelucire 44/14 | 9 |
| Talc | 1 |
| Magnesium stearate | 1 |

Naproxyn sodium was blended with microcrystalline cellulose, xanthan gum and hydroxypropylmethyl cellulose in a high shear mixer until a homogeneous mixture was obtained. This mixture was granulated with Gelucire isopropyl alcohol solution and dried in a fluid bed dryer to a loss on drying of about <2.0%. The dried granules were then passed through a sieve #14 mesh. The milled granules were blended with Carbopol 971P for 10 minutes, then with talc and magnesium stearate for 5 minutes in a V-blender. Finally, the treated granules were pressed into tablets using a rotary tablet press.

Example 7

Verapamil Hydrochloride ER Tablets

|  | % composition |
| --- | --- |
| Verapamil Hydrochloride | 50 |
| Microcrystalline cellulose | 14 |
| Xanthan gum | 10 |
| Hydroxypropylmethyl cellulose K100M CR | 14 |
| Compritol 888 ATO | 10 |
| Talc | 1 |
| Magnesium stearate | 1 |

Verapamil hydrochloride was blended with microcrystalline cellulose, xanthan gum, hydroxypropylmethyl cellulose and Compritol in a high shear mixer until a homogeneous mixture was obtained. This mixture was granulated with isopropyl alcohol and dry in fluid bed dryer to a loss on drying of about <2.0%. The dried granules were then passed through a sieve #14 mesh. The milled granules were blended with Carbopol 971P for 10 minutes, then with talc and magnesium stearate for 5 minutes in a V-blender. Finally, the treated granules were pressed into tablets using a rotary tablet press.

Example 8

Citalopram Hydrobromide

|  | % composition |
| --- | --- |
| Citalopram hydrobromide | 5 |
| Lactose anhydrous | 30 |
| Microcrystalline cellulose | 14 |
| Xanthan gum | 10 |
| Hydroxypropylmethyl cellulose K100M CR | 14 |
| Carbopol 971P | 5 |
| Gelucire 44/14 | 10 |
| Compritol 888 ATO | 10 |
| Talc | 1 |
| Magnesium stearate | 1 |

Citalopram hydrobromide was blended with microcrystalline cellulose, xanthan gum, hydroxypropylmethyl cellulose and Compritol in a high shear mixer until a homogeneous mixture was obtained. This mixture was granulated with Gelucire isopropyl alcohol solution and dry in fluid bed dryer to a loss on drying of about <2.0%. The dried granules were then passed through a sieve #14 mesh. The milled granules were blended with Carbopol 971P for 10 minutes, then with talc and magnesium stearate for 5 minutes in a V-blender. Finally, the treated granules were pressed into tablets using a rotary tablet press.

Although preferred embodiments have been described herein in detail, it is understood by those skilled in the art that variations may be made thereto without departing from the scope of the invention or the spirit of the appended claims.

What we claim:

1. A controlled release pharmaceutical device which provides sustained or pulsatile delivery of pharmaceutically active substances for a predetermined period of time, the device comprising;
   about 25 to 60% by weight microbial polysaccharide; and
   about 15 to 60% by weight cellulose ether.

2. The device of claim 1, wherein said device additionally comprises about 1 to 80% by weight pharmaceutical active.

3. The device of claim 2, wherein said pharmaceutical active is selected from the group consisting of naproxen, COX2 inhibitors, budesonide, venlafaxine, metoprolol, carbidopa, levodopa, carbamazepine, ibuprofen, morphine, pseudoephedrine, paracetamol, cisapride, pilocarpine, methylphenidine, nicardipine, felodipine, captopril, terfenadine, pentoxifylline, fenofibrate, aciclovir, zidovudine, moclobemide, potassium chloride, lamotrigine, citalopram, cladribine, loratadine, pancrelipase, lithium carbonate, orphenadrine, ketoprofen, procainamide, ferrous sulfate risperidone, clonazepam, lovastatin, simvastatin, pravachol, ketorolac, hydromorphone, ticlopidine, seligiline, alprazolam, divalproex and phenytoin.

4. The device of claim 3, wherein said device additionally comprises at least one agent selected from the group consisting of about 1 to 50% by weight crosslinked polymer; about 1 to 50% by weight lipophillic polymer; about 1 to 50% saturated polyglycolyzed glyceride and mixtures thereof.

5. The device of claim 4, wherein said device additionally comprises;
about 0.5 to 10% by weight lubricant.

6. The device of claim 5, wherein said lubricant comprises magnesium stearate or talc.

7. The device of claim 1, wherein said microbial polysaccharide is xanthan gum.

8. The device of claim 1, wherein said cellulose ether is hydroxypropylmethyl cellulose.

9. The device of claim 4, wherein said device additionally comprises about 1 to 65% granulating or tabletting aids.

10. The device of claim 9, wherein said granulating or tabletting aids are selected from the group consisting of silicon dioxide, microcrystalline cellulose, calcium phosphate, calcium sulphate, sodium laurel sulphate and silicified microcrystalline cellulose.

11. The device of claim 4, where said device is fabricated as a unit dose for pulsatile delivery of the pharmaceutical active or as a uniform matrix tablet for a sustained release of the pharmaceutical active.

12. The device of claim 11, wherein said device is formulated as a tablet having a hardness of about >5 Strong Cobb units and a friability of about <1%.

13. A pharmaceutical composition comprising:
over 25 to 60% by weight microbial polysaccharide;
about 15 to 60% by weight cellulose ether; and
about 1 to 80% by weight pharmaceutical active.

14. The composition of claim 13, wherein said composition additionally comprises at least of the agents selected the group consisting of about 1 to 50% by weight crosslinked polymer; about 1 to 50% by weight lipophillic polymer; about 1 to 50% saturated polyglycolyzed glyceride and mixtures thereof.

15. The composition of claim 14, wherein said composition additionally comprises about 0.5 to 10% by weight lubricant.

16. The composition of claim 15, wherein said composition additionally comprises about 1 to 65% granulating or tabletting aids.

17. A pharmaceutical composition comprising;
about 25 to 60% by weight xanthan gum;
about 15 to 60% by weight cellulose ether;
about 1 to 80% by weight pharmaceutical active;
at least one of the agents selected from the group consisting of;
about 1 to 50% by weight crosslinked acrylic acid polymer; about 1 to 50% by weight lipophillic polymer selected from the group consisting of glyceryl behenate, glyceryl palmitostearate and glyceryl stearate; about 1 to 50% saturated polyglycolyzed glyceride
about 0.5 to 10% by weight lubricant selected from the group consisting of at least one of magnesium stearate and talc; and
about 1 to 65% by weight granulating or tableting aids selected from the group consisting of silicone dioxide, microcrystalline cellulose, calcium phosphate, sodium laurel sulphate, calcium sulphate and silicified microcrystalline cellulose and mixtures thereof.

18. The composition of claim 17, wherein the pharmaceutical active is selected from the group consisting of COX2 inhibitors, budesonide, venlafaxine, metoprolol, carbidopa, levodopa, carbamazepine, ibuprofen, morphine, pseudoephedrine, paracetamol, cisapride, pilocarpine, methylphenidine, nicardipine, felodipine, captopril, terfenadine, pentoxifylline, fenofibrate, aciclovir, zidovudine, moclobemide, potassium chloride, lamotrigine, citalopram, cladribine, loratadine, pancrelipase, lithium carbonate, orphenadrine, ketoprofen, procainamide, ferrous sulfate risperidone, clonazepam, lovastatin, simvastatin, pravachol, ketorolac, hydromorphone, ticlopidine, seligiline, alprazolam, divalproex and phenytoin.

19. The controlled release pharmaceutical composition of claim 1, comprising about 4% by weight glipizide, about 20% by weight microcrystalline cellulose, about 40% by weight xanthan gum, about 33% by weight hydroxypropylmethyl cellulose, about 1% by weight silicone dioxide, about 1% by weight talc and about 1% by weight magnesium stearate.

20. A controlled release pharmaceutical composition comprising about 55% by weight naproxyn sodium, about 10% by weight microcrystalline cellulose, about 10% by weight xanthan gum, about 14% by weight hydroxypropylmethyl cellulose, about 9% by weight saturated polyglycolyzed glyceride, about 1% by weight talc and about 1% by weight magnesium stearate.

* * * * *